United States Patent [19]

Gordon

[11] Patent Number: 4,494,581
[45] Date of Patent: Jan. 22, 1985

[54] ISOLATION OF FORESTREAM AND MIDSTREAM PORTIONS OF COLLECTED URINE SAMPLES

[75] Inventor: Marvin Gordon, East Windsor, N.J.
[73] Assignee: Whitman Medical Corporation, Clark, N.J.
[21] Appl. No.: 467,905
[22] Filed: Feb. 18, 1983
[51] Int. Cl.³ .............................................. B65B 3/04
[52] U.S. Cl. ........................................ 141/1; 141/98;
141/286; 141/331; 141/392; 4/301; 73/863.41;
128/761; 210/531; 422/102
[58] Field of Search ...................... 141/1, 98, 331–345,
141/392, 285–300, 198–205, 115–127, 86;
73/863.41, 863.61, 863.51, 863.52; 422/102,
103, 58; 128/761; 210/531; 4/301, 144.1, 144.2,
144.3, 144.4, 450, 451, 462, 114.1

[56] References Cited

U.S. PATENT DOCUMENTS

| | | | |
|---|---|---|---|
| 3,583,388 | 6/1971 | Hovick | 128/761 |
| 3,635,091 | 1/1972 | Linzer et al. | 128/761 |
| 3,722,503 | 3/1973 | Hovick | 128/761 |
| 3,750,647 | 8/1973 | Gleason et al. | 128/761 |
| 3,830,107 | 8/1974 | Linzer | 128/761 |
| 3,943,770 | 3/1976 | McDonald | 128/761 |
| 3,982,898 | 9/1976 | McDonald | 128/761 |
| 4,040,791 | 8/1977 | Kuntz | 128/761 |
| 4,094,020 | 6/1978 | Franklin | 128/761 |
| 4,252,132 | 2/1981 | Kuntz | 128/761 |
| 4,276,889 | 7/1981 | Kuntz et al. | 128/761 |
| 4,331,162 | 5/1982 | Kuntz et al. | 128/761 |

FOREIGN PATENT DOCUMENTS 1574864  9/1980  United Kingdom ................ 128/761

*Primary Examiner*—Houston S. Bell, Jr.
*Attorney, Agent, or Firm*—Holman & Stern

[57] ABSTRACT

A forestream sample of a urine void is isolated from a subsequently collected midstream specimen by means of a valve controlled by material which swells to many times its original volume when exposed to urine. The material is disposed in a forestream receiving chamber having a normally open inlet aperture toward which void urine is directed by a funnel, or the like. Upon contact between the liquid and the material in the chamber, the material absorbs the liquid and swells to many times its original volume while forcefully urging a movable member against the aperture to block further entry of liquid into the chamber. Subsequently received liquid is redirected into a midstream specimen collection container. The void stream is initially received by a funnel having a discharge spout which terminates below the level of an overflow opening from which the subsequently received void portion is redirected into the midstream specimen container.

25 Claims, 8 Drawing Figures

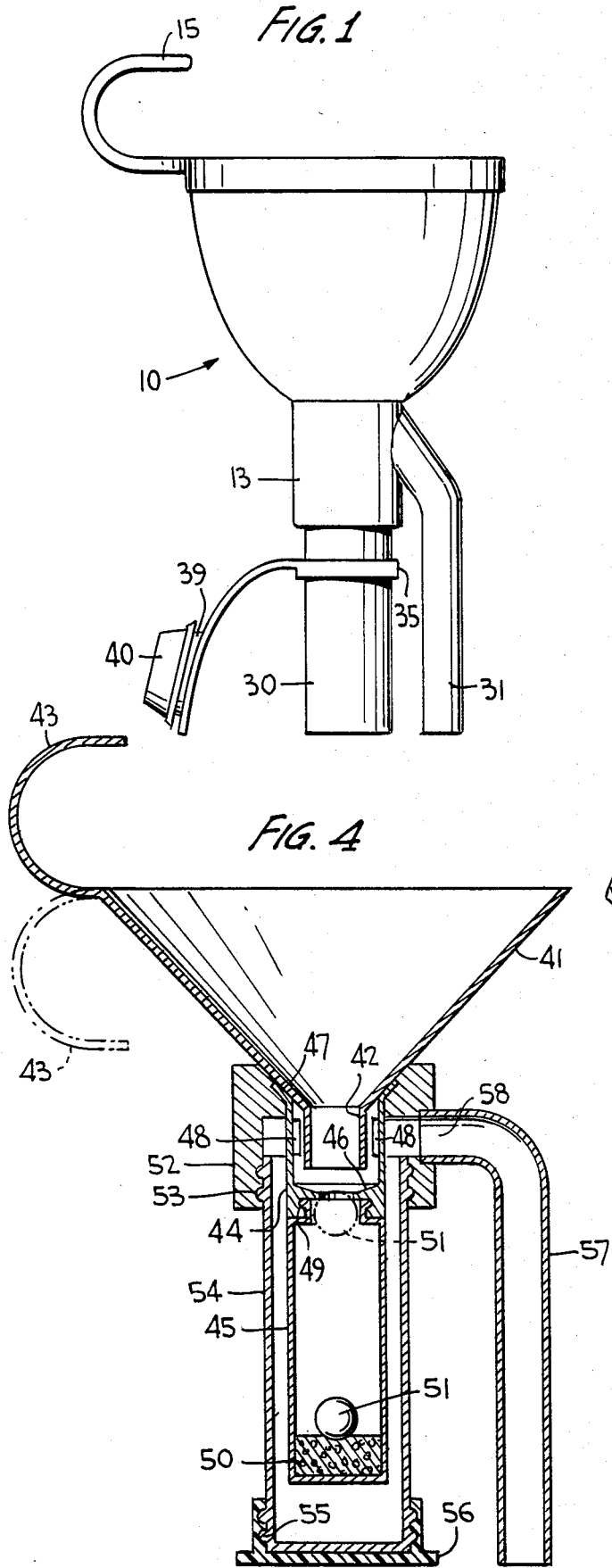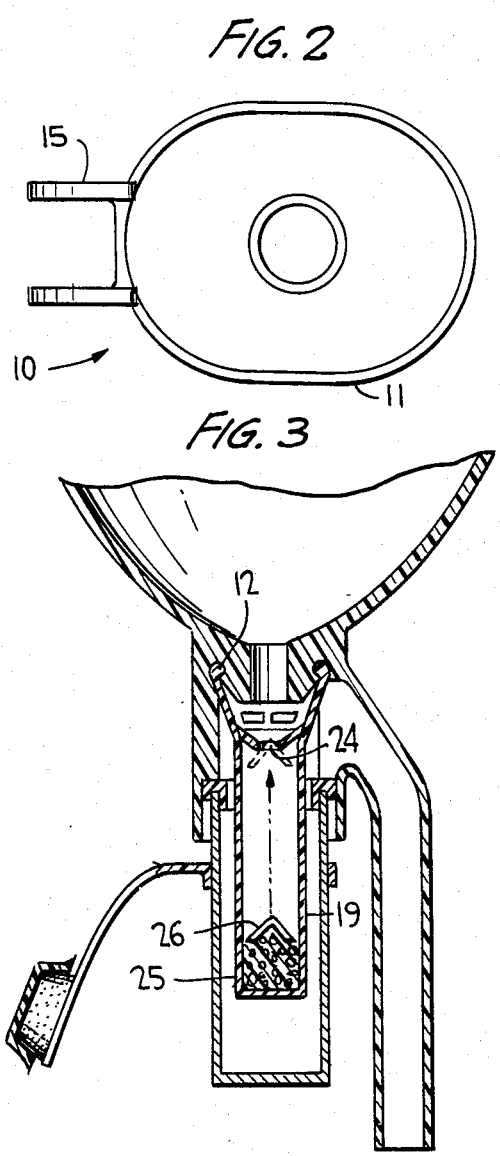

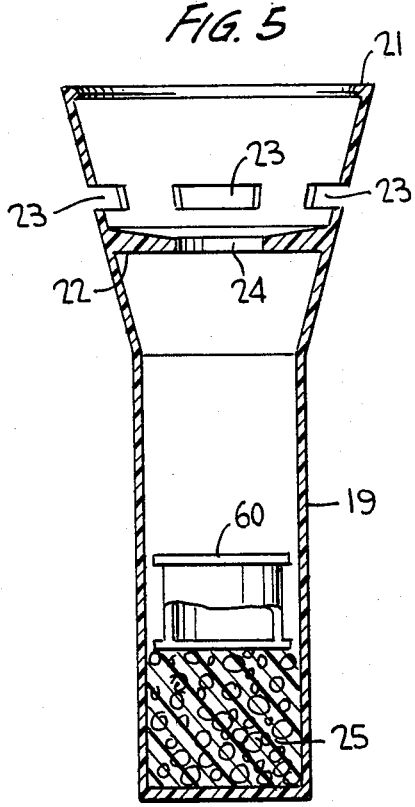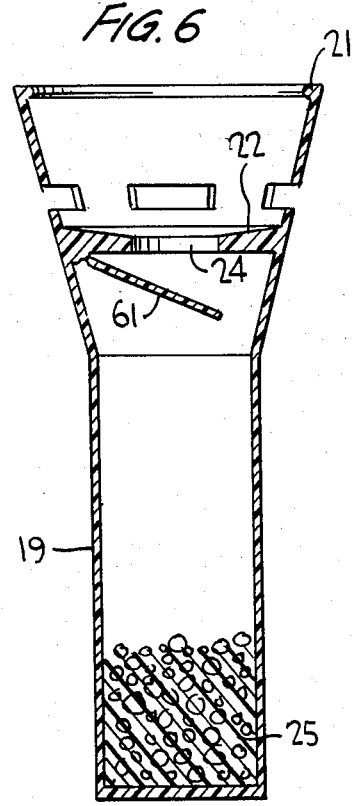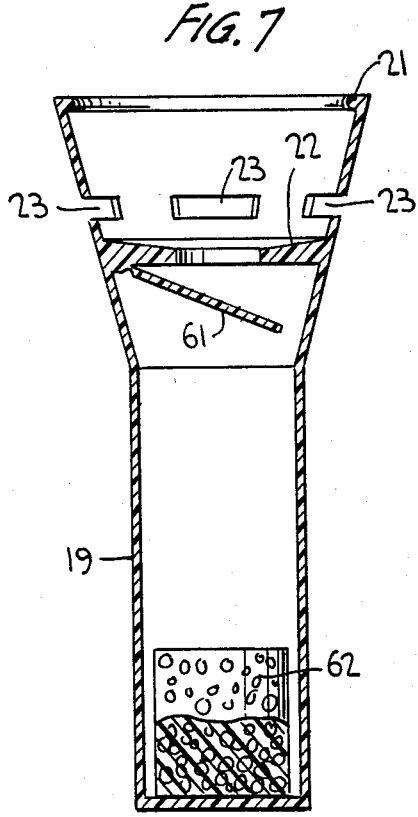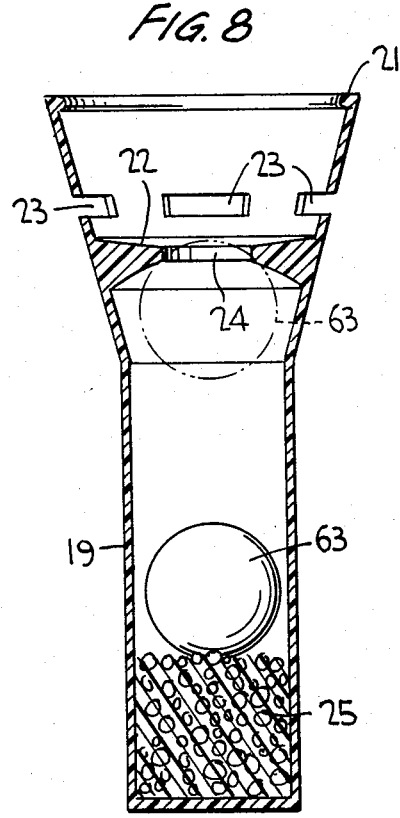

ISOLATION OF FORESTREAM AND MIDSTREAM PORTIONS OF COLLECTED URINE SAMPLES

BACKGROUND OF THE INVENTION

1. Technical Field

The present invention relates to a method and apparatus for collecting sterile samples of urine for analysis. More particularly, the present invention relates to positively isolating the forestream and midstream portions of a urine void so as to preclude contamination of the midstream portion by the forestream portion.

2. The Prior Art

In collecting urine samples for medical testing and analysis, it is important that the collected samples be as free from contaminants as possible. Contaminants in the urethra and other areas of the urinary tract render straightforward collection of sterile samples somewhat difficult. The problem of contamination is even greater for women patients than for men because of the location of the urethral opening just superior to the vaginal opening. Secretions and other contaminants which collect in the vaginal area, including the labia majora and labia minora, are a particularly troublesome source of urine specimen contamination. It is therefore desirable that the collected sample consist of a midstream portion of a urine void so that the urethra and other areas of the urinary tract, as well as the related portions of the vaginal area, can be flushed out by the initial or forestream portion of the void before the sample for analysis is passed for collection. However, midstream urine collection is not an easy procedure, primarily because it is difficult for a patient to interrupt a void stream so as to pass only part of the stream before the collecting sample. As a consequence, numerous devices have been proposed in the prior art for automatically collecting midstream portions of a urine void. Examples of these devices may be found in U.S. Pat. Nos. 3,583,388 (Hovick), 3,635,091 (Linzer, et al), 3,722,503 (Hovick), 3,750,647 (Gleason, et al.), 3,830,107 (Linzer, et al.), 3,943,770 (McDonald), 3,982,898 (McDonald), 4,040,791 (Kuntz), 4,094,020 (Franklin), 4,276,889 (Kuntz et al.) and 4,331,162 (Kuntz et al). In spite of these devices, problems still exist in the art of midstream urine collection.

Most, if not all, of the aforesaid prior art problems have been effectively solved by the method and apparatus described and illustrated in U.S. patent application Ser. No. 06/467,904 filed on the same date as the present patent application in the names of Joseph Lichtenstein and Vincent Valliancourt, which application is entitled "Sterile Urine Specimen Collection" and is assigned to the same assignee at the present invention. The disclosure in that patent application, which will hereafter be referred to as the Lichtenstein et al patent application, is expressly incorporated herein by reference in its entirety. One of the problems addressed by the Lichtenstein et al patent application is the intermixing of supposedly segregated forestream and midstream portions at a urine void in a collection apparatus. Specifically, many of the prior art midstream collection devices rely on directing the forestream portion of the void into a chamber and then diverting or overflowing the midstream portion into a specimen container when the urine level in the chamber reaches some predetermined level. In such devices, unless the assembly is held absolutely still, the forestream portion is jostled and tends to intermix to some degree with the diverted or overflowing midstream portion. This intermixing results in contamination of the midstream portion by contaminants in the forestream portion. Even when the device is held substantially still, flow currents exist which can carry contaminants from the forestream portion to the midstream portion. This problem is mitigated significantly by the collection device described in the aforesaid Lichtenstein et al patent application. More particularly, in that device, a solid body of urine-absorbent material is placed in a forestream collection chamber to effectively immobilize the liquid and drastically reduce the aforesaid currents. However, there still remains a liquid/air interface at the top of the forestream collection chamber to which the midstream portion of a void is directed before it is overflowed into the midstream specimen collection container. Thus, even though the Lichtenstein et al approach severly reduces the contamination as compared to prior art devices, it is still possible that the contacts between the midstream portion and the top surface of the forestream portion can result in contamination of the midstream portion.

Another problem which is not fully solved in the aforesaid Lichtenstein, et al patent application concerns stearing or directing the initial or forestream portion of the void so that it does not flow toward the overflow outlets, but instead flows directly into the forestream collection chamber. Specifically, the Lichtenstein et al device includes a void-receiving funnel having a discharge spout which terminates at a level above the overflow outlets, but is of smaller diameter than the wall in which the overflow outlets are defined. Thus, if the unit is oriented substantially vertically, the liquid discharged from the funnel is directed into the forestream chamber and not through the overflow outlets. However, it is not always possible for the unit to be held substantially vertically in use and, under such circumstances, the discharge from the funnel can be directed through the overflow outlets.

SUMMARY AND OBJECTS OF THE INVENTION

It is therefore an object of the present invention to provide a method and apparatus which positively isolates the forestream and the midstream portions of void urine samples. While the preferred embodiment of the invention is described and illustrated as an improvement of the apparatus described and illustrated in the aforesaid Lichtenstein, et al patent application, it is the object of the present invention to positively isolate the forestream and midstream void portions in substantially any midstream collection device.

It is a further object of the present invention to provide an improved method and apparatus for collecting a midstream sample of a urine void in a manner which positively avoids contamination of the collected sample by the forestream portion of the void.

It is a more specific object of the present invention to protect against intermixing of forestream and midstream portions of a urine void in a midstream sample collection device, and particularly, such intermixing which would result from normal flow currents and turbulence in the received forestream portion.

Still another object of the present invention is to provide a device for collecting a midstream portion of a urine void wherein the discharge from a receiving funnel is precluded from being issued directly toward the forestream collection chamber overflow outlet for all practical orientations of the device.

In accordance with the present invention, intermixing of the received forestream sample with the subsequently received midstream portion is achieved by forcefully closing a valve in a forestream receiving chamber. More specifically, a urine-absorbent material, which swells to many times its volume when wetted, is disposed in a forestream receiving chamber. A movable valve member is disposed above the dry material and is forced by the swollen wetted material against an inflow opening for the chamber. The movable valve member and the inflow opening are contoured to provide a positive closure of the inflow opening when the absorbent material swells to a predetermined volume. The swollen material continuously urges the valve member to its closed position for the remainder of the void procedure, thereby isolating the initially received forestream portion from the subsequently received void portion. When the valve is closed, subsequently received void portions, directed toward the inflow opening, are directed to a midstream specimen collection container through an overflow outlet.

The absorbent material may be a solid body, a plurality of pellets, a powder, or other convenient form. The valve member may take any form consistent with the requirement that it be capable of positively closing the inflow opening when forced against the opening by the swellable material. Examples of a movable member are hinged flaps, hollow spheres, hollow cylinders, conical members, etc. It is preferred that the movable valve member be capable of floating in the urine liquid.

The void is received by the unit in a funnel having a discharge opening disposed below the overflow outlet so that the orientation of the device, in use, can approach horizontal without the funnel discharge being issued directly toward the overflow outlet.

BRIEF DESCRIPTION OF THE DRAWINGS

These and other objects, features and many of the attendant advantages of the present invention will be better understood upon a reading of the following detailed description when considered in connection with the accompanying drawings wherein like parts in each of the several figures are identified by the same reference numerals, and wherein:

FIG. 1 is a side view in elevation of one embodiment of a midstream specimen collection apparatus according to the present invention;

FIG. 2 is a top view of the embodiment of FIG. 1;

FIG. 3 is a broken view in vertical section of the embodiment of FIG. 1 showing one form of valving mechanism according to the present invention;

FIG. 4 is a view in vertical section of another midstream collection unit embodiment according to the present invention;

FIG. 5 is a view in vertical section of a modified form of a valving mechanism according to the present invention;

FIG. 6 is a view in vertical section of another modified form of valving mechanism according to the present invention;

FIG. 7 is a view in vertical section of still another modified form of a valving mechanism according to the present invention; and FIG. 8 is a view in vertical section of a third and modified form of valving mechanism according to the present invention.

DESCRIPTION OF THE PREFERRED EMBODIMENTS

Referring specifically to FIGS. 1, 2 and 3 of the accompanying drawings, a midstream specimen collection assembly is generally designated by the reference numeral 10. A urine stream collecting or receiving funnel 11 has a generally oval opening at its top and a depending annular sleeve 13 at its bottom. A handle 15 is secured to, and is preferably integrally formed with, funnel 11 at the lip of the top opening. Handle 15 is disposed along the major axis of the oval opening (i.e. at a side having a smaller radius of curvature) so that the opposite side may be easily positioned between the patient's legs to receive a urine void stream. Handle 15 has a generally C-shaped configuration with its open side facing radially inward. The handle 15 illustrated in FIGS. 1 and 2 is bent upward to be located above the upper lip of the funnel; however, it should be understood that the handle may just as readily be bent downward so that its distal and faces the outer periphery of the funnel. In either case, with this handle configuration, a patient can readily hold the unit with his or her index finger inside the open C-shaped configuration and his or her thumb on the top leg of the handle; alternatively, the handle may be grasped with the thumb inside the handle opening and two or three fingers on the outer handle surface. The oval funnel configuration, apart from facilitating deployment of the unit in use, minimizes bulk and maximizes the target area for the void stream, particularly for female patients.

Interiorly of sleeve 13 and above its lower end, there is a funnel discharge outlet 17 which is preferably disposed at the radial center of the funnel to discharge all liquid received through the open upper end of the funnel. A forestream collection tube 19 for the initial or forestream portion of the void urine is disposed directly below discharge outlet 17 to receive all liquid discharged through that outlet. In the illustrated embodiment, discharge outlet 17 takes the form of an annular projection extending downwardly within outer sleeve 13. The juncture between the outer surface of outlet 17 and the inner surface of sleeve 13 is contoured to receive an annular lip 21 of forestream collection tube 19 in a snap-fit engagement. The upper portion of tube 19 includes a downwardly tapered section which is bounded at its top by lip 21. The bottom portion of tube 19, which is axially longer than the tapered portion, is generally cylindrical and projects concentrically down through sleeve 13. A plurality of angularly spaced overflow outlet openings 23 are defined in tube 19 in its tapered upper portion. Lip 21 is secured about the discharge outlet 17 such that the bottom of the discharge outlet terminates at a level which is axially between lip 21 and openings 23 in tube 19. The opening of discharge outlet 17 has a smaller diameter than the diameter of the tapered portion of tube 19 at overflow openings 23 so that liquid discharged through outlet 17 cannot flow directly into outlet 23.

A generally annular top wall 22 for tube 19 is disposed interiorly of the tapered upper tube portion at a height below overflow openings 23. In describing wall 22 as "generally annular" it should be noted that a more apt characterization for wall 22 illustrated in FIG. 3 would be frusto-conical. In this regard, it is desirable, although not necessary, that the top surface of wall 22 be sloped downwardly toward the chamber inflow opening 24 which is defined through wall 22. The slope prevents liquid from collecting on top wall 22 so that the top surface acts as a funnel. Top wall 22 may be formed integrally with tube 19 or it may be secured by adhesive, or the like, along its peripheral border to the tube interior. The portion of tube 19 below wall 22 is closed and constitutes a collection chamber for the forestream or initial portion of a urine void stream.

Pellets 25 of urine-absorbent material are disposed at the bottom of the chamber in tube 19. The material has the property of being extremely urine-swellable while being insoluble in urine. In other words, when pellets 25 are exposed to and absorb urine in the forestream collection chamber, the pellets swell to many times their original dry volume. Many such products which exhibit these characteristics are available commercially. One example is the SGP Absorbent Polymer (E.G. Models SGP 104 SGP 502S, SGP 147) sold by Henkel Corporation of Minneapolis, Minn. Typically, this product absorbs 80–90 milliliters per gram of urine and is composed of starch and a synthetic polymer made up of acrylamide and sodium or potassium acrylate. Proportions of starch and polymer are approximately 2:3; proportions of acrylate and acrylamide are approximately 3:1. Another useful swellable material is carboxymethyl cellulose, interspersed with rayon or cotton, sometimes referred to as super absorbent cellulose.

A movable valve member 26 is disposed in the chamber portion of tube 19 on top of dry pellets 25. In the embodiment of FIG. 3, the movable member is of conical configuration with its apex pointing upward. Importantly, the horizontal cross-section of member 26 is circular, or at least the same as the configuration of inflow opening 24 in top wall 22. This permits member 26 to make complete peripheral contact with inflow opening 24 and thereby seal that opening when member 26 is pushed upwardly against wall 22 by swollen pellets 25. In other words, when the forestream portion of the urine void is received in the collection chamber of tube 19, it is absorbed by the pellets which swell and force member 26 into sealing engagement with inflow opening 24. In order to prevent overturning of member 26 in the chamber, that member may be provided with a cylindrical bottom portion having a diameter which is slightly smaller than or equal to the inner diameter of tube 19 in the chamber section. Importantly, there should be no significant frictional engagement beteween member 26 and chamber 19 which would prevent or slow the raising of the member 26 under the force of the expanding or swelling pellets 25. The pressure exerted by the swollen or expanded pellets 25 on member 26 forcefully urges member 26 against wall 22 and positively seals the inflow opening 24.

An annular downwardly-facing shoulder 27 is defined on the inner wall of annular sleeve 13. An annular rubber seal 29, having an inverted generally U-shaped vertical cross-section, has its base and one leg secured to shoulder 27 and the inner wall of sleeve 13, respectively. The open leg of the seal 29 receives the annular upper edge of the open-top midstream specimen collection container 30 having a generally cylindrical configuration. Container 30 is open at its top but is otherwise enclosed. When received in seal 29, container 30 is positioned in radially-spaced concentric relation about the lower portion of forestream collection tube 19 which projects a considerable axial distance into the container. The friction-fit engagement of the container 30 in seal 29 permits the container to be disconnected or disassociated from the funnel and tube 19 by merely pulling downward on the container while slightly rotating it about its longitudinal axis.

With midstream specimen collection container 30 connected in seal 29, overflow outlet openings 23 in tube 19 are positioned above the top of container 30 and above the annular space subsisting between the radially inner portion of seal 29 and the exterior of tube 19. This annular space serves as an annular ingress opening for liquid which overflows tube 19 via openings 23.

A drain passage 31 has its upper or inlet end extending generally downward and away from the annular space above seal 29 and adjacent overflow outlet 23 of tube 19. A radially inner side of drain passage 31 forms a weir-like structure 33 over which flows the overflow liquid from midstream specimen collection container 30. Drain passage 31 takes the form of a tube, the lower portion of which extends downwardly, parallel to container 30, on the side of the assembly 10 which is diametrically opposed to that on which handle 15 is located.

A plastic or rubber retainer ring 35 is secured about container 30 in a friction-fit or permanent engagement, if desired. A flexible strap 37 extends radially from retainer ring 35 and has a cap 39 secured to its upwardly facing side. A cover 40 hermetically seals cap 39 which takes the form of a plug that can be inserted into the upper end of container 30 to seal the container when the latter is removed from seal 29.

In use, the collection assembly 10 is grasped by handle 15 so that the upper end of funnel 11 is positioned to receive a void urine stream. The initial or forestream portion of the void is discharged past overflow outlet 23 into forestream collection tube 19 where it is absorbed by pellets 25 which swell in a matter of a few seconds to many times their size. The swollen pellets force valve member 26 into a closure position against wall 22 with the apex of member 26 projecting into inflow opening 24. Subsequent liquid discharged through funnel outlet 17 quickly fills the small volume above wall 22 up to overflow outlet 23 from which the liquid overflows and falls into midstream specimen collection container 30. After container 30 has been filled, further overflow through openings 23 flows over wier-like structure 33 and down through drain tube 31. It is presumed that the collection procedure is performed over a commode or other waste receptacle so that the terminal portion of the void which is drained via tube 31 can be disposed of properly.

It is to be noted that the volume of urine collected in midstream collection container 30 is less than the capacity of this container by an amount equal to the outer volume of the lower portion of tube 19 which extends into container 30. The outer volume of this lower portion of tube 19 is greater than the volume of the annular space which exists between the very top of container 30 and the tip of weir-like structure 33. This permits the void liquid which resides in this annular space to fall into container 30 when the container is pulled away from the assembly and tube 19 is withdrawn from within the container. If the liquid in the annular space above container 30 could not be accomodated within this volume previously occupied by tube 19, this liquid would spill or leak out of the assembly when the container is disconnected from the seal. Therefore, the positioning of tube 19 within container 30 serves not only to render the assembly compact and easy to handle, but also to eliminate spillage and leakage upon removal of the specimen container.

The valve mechanism provided by pellets 25, valve member 26 and inflow opening 24 results in complete isolation of the original or forestream portion of a urine void from the subsequently received midstream portion which overflows through outlets 23. The sealing of chamber 19 prevents drying out and shrinkage of the swollen pellet material 25 during a void procedure so that the pressure effecting the valve closure is not abated and isolation of the forestream and midstream portions is not disturbed.

When voiding is terminated, the specimen container 30 is easily removed from seal 29 and then capped by plug 39 after removal of cover 40 from the plug. The remainder of the assembly may then be thrown away. Alternatively, the remainder of the assembly may be cleaned and sterilized and then re-used with another container 30; however, disposability is a desirable and preferred feature of the present invention.

Another embodiment of the invention is illustrated in FIG. 4 of the accompanying drawings to which specific reference is now made. A void receiving funnel 41 is illustrated as having a generally conical configuration with a generally cylindrical discharge port 42 at its lower end. Alternatively, the funnel may have an oval upper lip with a configuration similar to that illustrated for funnel 11 in FIGS. 1 and 2. Funnel 41 has a generally C-shaped handle 43 projecting from its top lip with the convex sides of the handle facing generally radially outward from the funnel. As illustrated, the handle may curve either above or below the top lip of the funnel.

A forestream receiving member 44 has a generally tubular configuration. As illustrated, the entire tube 44 is cylindrical except for a small upper lip 47 which diverges upwardly to match the outer configuration of an abutting portion of the funnel periphery. One or more overflow outlet openings 48 are defined through receiving tube 44 at a location below lip 47. The lowermost part of discharge port 42 of the funnel projects below openings 48 so that liquid issued from port 42 cannot flow directly toward overflow openings 48, even if the overall device is oriented almost horizontally as opposed to the illustrated vertical orientation. Tube 44 has an annular interior wall 46 proximate its lower end. Wall 46 has a top surface which slopes in a funnel-like manner toward a central opening which serves as the inflow opening for a forestream receiving chamber 45. Annular wall 46 also serves as the female part of a snap-fit annular connector by which the forestream receiving chamber is detachably secured to tube 44.

The forestream receiving chamber 45 is a generally cylindrical chamber which is fully enclosed except for an open upper end. The upper end of chamber 45 includes an annular lip 49 contoured to mate in snap-fit engagement with the female portion of the connector formed in annular wall 46 of tube 44. Urine-absorbent material 50 of pellet, powder or block form, is disposed in chamber 45. This material is the same or similar to material 25 illustrated in FIG. 3 in that it swells to many times its volume when it absorbs urine. A valve member 51, illustrated in FIG. 4 in the form of a sphere, is positioned atop material 50 so as to be forced against and seal the central opening in wall 46. In this regard, spherical member 51 must have a diameter which is greater than the diameter of the aperture in wall 46. In addition, spherical member 51 should be capable of floating in urine.

An annular connector 52 is configured to sit concentrically about tube 44 and discharge port 42. The upper end of connector 52 includes a frusto-conical surface in contact with the outer peripheries of funnel 41 and lip 47 of tube 44. The funnel 41, connector 52 and lip 47 are ultrasonically welded or otherwise joined together at their contact surfaces to form a rigid inseparable unit. The lower portion of the interior of connector 52 is threaded at 53 to receive the externally threaded top of a midstream specimen collection container 54. The container 54 is a cylinder which is closed except for its open upper end. When the container is threadedly engaged to connector 52, and when chamber 45 is engaged to tube 44, container 54 is disposed concentrically about chamber 45. The lower portion of container 54 is externally threaded at 55 in a manner identical to the upper end of the container. Threaded portion 55 is employed to threadedly engage a cap 56 until the cap is needed for deployment to seal the container. When the container 54 is filled and disengaged from connector 52, cap 56 can be removed from threaded portion 55 and secured in threaded engagement to the container top to seal the collected midstream specimen in the container.

A flexible overflow or drain tube 57 is inserted by friction fit into a radially-extending through hole or port 58 defined through connector 52. Hole 58 is positioned substantially adjacent overflow openings 48 and above the top of container 54.

In operation, void urine is received by funnel 41 and discharged by port 42 toward the aperture in annular wall 46. The liquid flows into chamber 45 where it is absorbed by material 50. The material swells until it forces spherical member 51 into sealing engagement with the aperture in wall 46. Liquid thereafter discharged from port 42 fills the portion of tube 44 disposed above wall 46 and then overflows through openings 48. The initial overflow falls into container 54 and constitutes the midstream specimen which is collected. When container 54 is filled, subsequent overflow is conducted out of the unit via drain tube 57. When the void is terminated, container 54 is unscrewed from connector 52 and sealed with cap 56. The midstream specimen contained in container 56 is then sent for analysis.

The embodiment illustrated in FIG. 5 shows the forestream collection tube 19 of the embodiment of FIG. 3 with a different valving configuration. Specifically, the movable member 60 takes the form of a hollow closed-ended cylinder of slightly smaller diameter than the inner diameter of tube 19. The diameter of cylinder 60 is sufficiently large to assure that it fully covers aperture 24 in chamber top wall 22 when swellable material 25 forces the cylinder against wall 22. Wall 22 is shown in FIG. 5 without a sloped top surface; however, it is to be understood that this feature may be provided if desired.

In the embodiment of FIG. 6, the movable member is a panel or door-like member 61 hinged to the underside of wall 22. The term "hinged" is used to mean a "living hinge"-type connection wherein member 61 is formed integrally with wall 22 and is resiliently biased downward and away from aperture 24. When material 25 absorbs liquid and swells sufficiently, panel 61 is forced against the underside of wall 22 and seals aperture 24. A similar configuration is illustrated in FIG. 7 except that the swellable material 62 is illustrated as a solid block rather than pellets or powder.

The embodiment of FIG. 8 illustrates the movable valve member as a ball 63 which can be forced by the swellable material 25 to block aperture 24. Ball 63 should float in urine and must have a larger diameter than aperture 24.

Typically, the device of the present invention is used to collect a midstream specimen having a volume of approximately 70 cc. The forestream portion volume is usually on the order of 20–30 cc. The sizes of the midstream specimen container and the forestream collection chamber are chosen accordingly. In the embodiment of FIG. 4, discharge outlet port 42 for funnel 41 is typically ½ inch in diameter; the forestream collection chamber 45 is typically ¾ inch in diameter and 2¾ inches in height; the midstream specimen container 54 is typically 1¼ inch in diameter and 3½ inches in height; tube 44 is typically ¾ inch in diameter and 1 inch in height; connector 52 is typically 1¾ inch in outside diameter and 1¼ inch in height; the aperture in wall 46 is typically ¼ inch in diameter; and the diameter of sphere 51 is typically ⅜ inch. These dimensions are, of course, only examples of a typical embodiment and should not be construed as limitations on the scope of the invention.

The invention as described herein provides for complete isolation of the forestream and midstream portions of a collected urine void by positively sealing the forestream collection chamber. In addition, by disposing the lower end of the discharge port 42 (FIG. 4) below the overflow openings 48, direct flow of liquid from port 42 into openings 48 is avoided for a wide variety of orientations of the collection device.

Having described several embodiments of the new and improved method and apparatus for isolating forestream and midstream portions of collected urine samples, it is believed that other modifications, variations and changes will be suggested to those skilled in the art in light of the above teachings. It is therefore to be understood that all such variations, modifications and changes are believed to fall within the scope of the invention as defined in the appended claims.

What is claimed is:

1. Apparatus for collecting a midstream portion of void urine, said apparatus comprising:
    a midstream specimen collection container having an inlet opening;
    a forestream receiving chamber having an inflow opening defined therein;
    absorbent means disposed in said forestream receiving chamber and responsive to received urine for swelling to many times its original volume;
    closure means responsive to swelling of said absorbent means to a predetermined volume for blocking said overflow opening of said forestream receiving chamber;
    liquid receiving means for receiving a void urine stream and discharging the received urine generally toward said inflow opening in said forestream collection chamber; and
    means responsive to blocking of said inflow opening of said forestream receiving chamber for flowing liquid discharged by said liquid receiving means into said midstream specimen collection container.

2. The apparatus according to claim 1 wherein said inflow opening of said forestream receiving chamber is an aperture defined through a wall of said chamber and wherein said closure means is a movable object disposed in an open position above said absorbent means and below said aperture in said chamber when said absorbent means is dry, said object being moved by said absorbent means when the absorbent means swells to said predetermined volume so as to be forced into a closed position wherein the object blocks said aperture.

3. The apparatus according to claim 2 wherein said aperture is generally circular and said movable object is a ball which floats in urine and has a radius greater than the radius of said aperture.

4. The apparatus according to claim 2 wherein said wall of said chamber is a top wall, wherein said aperture is generally circular, and wherein said movable object is a generally conical member having an apex which projects through said aperture in said closed position.

5. The apparatus according to claim 4 wherein said wall is a top wall of said chamber, and wherein said movable object floats in urine and includes a top surface which abuts said top wall in said closed position to block said aperture.

6. The apparatus according to claim 5 wherein said object is a hollow cylindrical member having a longitudinal axis oriented generally vertically in said chamber when said apparatus is in use, said hollow cylindrical member being closed at least at its top by a wall which includes said top surface.

7. The apparatus according to claim 6 wherein said chamber is generally cylindrical and has an interior diameter which is only slightly greater than the diameter of said cylindrical member to permit free vertical movement of said cylindrical in said chamber without substantial rotation of the cylindrical member about any axis perpendicular to said longitudinal axis.

8. The apparatus according to claim 2 wherein said movable object is a flap hinged to said wall in said chamber and normally biased away from said aperture, said flap being positioned to be pivoted by the swollen absorbent means to block said aperture.

9. The apparatus according to claim 2 wherein said wall of said chamber is a top wall having an exposed top surface which slopes toward said aperture to prevent collection of liquid on said top surface.

10. The apparatus according to claim 2 wherein said absorbent means comprises a plurality of small pellets of material which is insoluble in urine but which swells when it absorbs urine.

11. The apparatus according to claim 2 wherein said absorbent means comprises a solid body of material which is insoluble in urine but which swells when it absorbs urine.

12. The apparatus according to claim 2 wherein said absorbent means is a material comprising a mixture of starch and a synthetic polymer made up of acrylamide and an acrylate.

13. The apparatus according to claim 12 wherein the proportion of starch to polymer in said material is approximately two to three, and wherein the proportion of acrylate to acrylamide in said material is approximately three to one.

14. The apparatus according to claim 2 wherein said forestream receiving chamber is a bottom portion of a generally tubular member having an upper end above said chamber through which urine discharged from said receiving member flows toward said inflow opening, said upper end having an overflow outlet means defined therethrough for overflow in urine received in said upper end when said inflow opening is closed.

15. The apparatus according to claim 14 wherein said forestream receiving chamber, except the aforesaid inflow opening, is fully enclosed.

16. The apparatus according to claim 2 wherein said forestream receiving chamber is part of a generally tubular member having an upper portion extending above said chamber inflow opening, a closed lower end defining the bottom of said chamber and an overflow outlet means disposed in said upper portion for overflowing liquid entering said upper portion when said inflow opening is blocked;

said apparatus further comprising means for selectively securing said midstream specimen collection container relative to said forestream receiving chamber with the closed lower end of said forestream receiving chamber extending into said midstream collection container through said inlet opening and with said overflow outlet means disposed outside and generally above said midstream specimen collection container.

17. The apparatus according to claim 16:

wherein said inlet opening of said midstream specimen collection container is sufficiently wider than the periphery of the lower end of said tubular member extending therethrough to provide an inlet flow path into said midstream specimen collection container for liquid which overflows said overflow outlet means; and wherein said apparatus further comprises drain means for receiving subsequent overflow of liquid from said inlet opening of said midstream specimen collection container.

18. The apparatus according to claim 17 wherein said liquid receiving means is a funnel having a generally oval and relatively wide inlet and a small discharge opening projecting into said upper portion of said tubular member to a level below said overflow outlet means.

19. The apparatus according to claim 17 wherein said drain means is a flow passage which conducts said subsequent overflow of liquid downwardly and externally of said apparatus.

20. The apparatus according to claim 17 wherein said drain means comprises a reservoir for collecting said subsequent overflow of liquid.

21. The apparatus according to claim 17 further comprising:

a cap which is deployable to engage said midstream specimen collection container to seal said inlet opening when the midstream specimen collection container is removed relative to said forestream receiving chamber; and means for removably attaching said cap in a medically sterile manner to said apparatus for subsequent removal and deployment to engage said midstream specimen collection container.

22. Apparatus for collecting a midstream portion of void urine, said apparatus comprising:

a midstream specimen collection container having an inlet opening;

a forestream receiving member having an upper end, an inflow opening defined below said upper end, a closed lower end and overflow outlet means disposed above said inflow opening in said upper end for overfowing liquid entering said upper end when said inlow opening is blocked;

means for selectively securing said midstream specimen collection container relative to said forestream receiving member with the closed lower end of said forestream receiving member extending into said midstream collection container through said inlet opening and with said overflow outlet means disposed outside said midstream specimen collection container;

liquid receiving means for receiving a void urine stream and discharging the received urine toward said inflow opening in said forestream receiving member;

urine-absorbent material disposed in said forestream receiving member, said material having the characteristic of swelling to many times its size upon absorbing liquid;

closure means disposed in said forestream receiving member above said urine-absorbent material and positioned so as to be forced against and block said inflow opening when said urine-absorbent material swells to a predetermined volume;

wherein said inlet opening of said midstream specimen collection container is sufficiently wider than the periphery of the lower end of the forestream receiving member extending therethrough to permit an inlet flow path into said midstream specimen collection container for liquid which overflows from said overflow outlet means; and drain means for receiving subsequent overflow of liquid from said inlet opening of said midstream specimen collection container.

23. Apparatus for collecting midstream portion of void urine, said apparatus comprising:

a urine stream receiving member having a relatively wide inlet opening for receiving void urine, a relatively small discharge opening for discharging received urine, and a contour which directs all urine received at said inlet opening toward said discharge opening;

a forestream receiving member having an upper end, a controlled opening disposed below said upper end to receive urine discharged from said discharge opening of said receiving member, an overflow outlet means disposed at a predetermined height in said forestream receiving member and above said controlled opening for overflowing all urine received through said upper end when the urine level therein reaches said predetermined height or said controlled opening is closed, said forestream receiving member being fully enclosed below said controlled opening;

a selectively detachable midstream specimen collection container having an inlet opening arranged to receive initial overflow of urine through said overflow outlet means;

drain means arranged to receive subsequent overflow of urine through said overflow outlet means after the level of urine in said specimen collection container reaches a predetermined level; and connection means for selectively detaching the specimen collection container from said apparatus.

24. A method for collecting a midstream specimen of void urine comprising the steps of:

directing a forestream portion of a urine void into a chamber through an inlet opening;

absorbing urine received in said chamber with a material which swells significantly upon absorbing liquid;

forcefully closing said inlet opening of said chamber under the impetus of the swelling of said material; and directing a subsequent portion of said urine void into a midstream specimen container after said inlet opening is closed.

25. Apparatus for collecting a midstream portion of void urine, said apparatus comprising:

a forestream receiving member having an overflow outlet disposed to overflow liquid from said member after said member has received a predetermined volume of initial void urine;

midstream collection means for receiving said midstream portion of void urine after said forestream receiving member has received said predetermined volume of initial void urine; and a generally funnel-shaped member having a relatively wide inlet and a relatively narrow discharge portion, said discharge portion extending into said forestream receiving member to a level below said overflow outlet.

* * * * *